United States Patent [19]
Kim et al.

[11] Patent Number: 6,072,051
[45] Date of Patent: Jun. 6, 2000

[54] NUCLEOSIDE DERIVATIVES AND PROCESS FOR PREPARING THE SAME

[75] Inventors: Jung Woo Kim, Seoul; Koo Hun Chung, Kyeonggi-do; Soon Kil Ahn, Seoul; Hoe Joo Son, Kyeonggi-do; Byeong Seon Jeong, Seoul, all of Rep. of Korea

[73] Assignee: Chong Kun Dang Corp., Seoul, Rep. of Korea

[21] Appl. No.: 09/068,220

[22] PCT Filed: Nov. 1, 1996

[86] PCT No.: PCT/KR96/00189

§ 371 Date: May 1, 1998

§ 102(e) Date: May 1, 1998

[87] PCT Pub. No.: WO97/16456

PCT Pub. Date: May 9, 1997

[30] Foreign Application Priority Data

Nov. 2, 1995 [KR] Rep. of Korea ........................ 95-39340

[51] Int. Cl.[7] .......................... C07H 19/06; C07H 19/16; C07H 19/67; C07H 16/73; C07H 19/167

[52] U.S. Cl. .................. 536/27.1; 536/27.11; 536/27.21; 536/27.22; 536/28.4; 536/28.5; 544/253; 544/264; 544/269

[58] Field of Search ............................... 536/22.1, 26.12, 536/26.8, 27.1, 27.14, 27.6, 27.62, 28.1, 27.22; 544/253, 269, 264

[56] References Cited

FOREIGN PATENT DOCUMENTS 0 515 156 A1   11/1992   European Pat. Off. .
WO 92/06102    4/1992    WIPO .

OTHER PUBLICATIONS

Hammerschmidt, F., et al., "Convenient Route to D–apio–β–D–furanosyl– and 2'–deoxyapio–β–D–furanosyl Nucleosides," Chemical Abstracts, 123: 257236f (Nov. 6, 1995).

Doong, S.L., et al., "Inhibition of the Republican of Hepatitis B Virus In Vitro by 2', 3'–dideoxy–3'–thiacytidine and Related Analogues," Proc. Nat'l. Acad. Sci., vol. 88, pg/ 8495–8499 (Oct. 1991).

Lin, T.S., et al., "Antiviral Activity of 2', 3'–dideoxy–β–L–5–Fluourcytidine (β–L–FddC) and 2', 3'–dideoxy–β–L–Cytidine (β–L–ddC) Against Hepatitis B Virus and Human Immunodeficiency Virus Type 1 In Vitro," Biochemical Pharmacology, vol. 47, No. 2, pp. 171–174 (1984).

*Primary Examiner*—James O. Wilson
*Assistant Examiner*—Howard Owens
*Attorney, Agent, or Firm*—Heslin & Rothenberg, P.C.

[57] ABSTRACT

According to the present invention, provided are novel nucleoside derivatives having antiviral activity, in particular, anti-HBV (anti-Hepatitis-B Virus) activity, represented by general formula (I), wherein $R_1$ represents hydrogen, phosphate, phosphonate, alkyl or acyl; $R_2$ represents alkoxy or halogen; $R_3$ represents substituted or non-substituted pyrimidine or purine base; and X represents O, S, SO or $SO_2$; pharmaceutically acceptable salts thereof, and processes thereof. As the compound (I) has two or more asymmetric carbon atoms, all possible stereoisomers and mixtures thereof are included in the scope of the present invention.

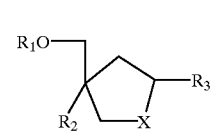

(I)

15 Claims, No Drawings

NUCLEOSIDE DERIVATIVES AND PROCESS FOR PREPARING THE SAME

This is a 371 of PCT/KR96/00189 filed Nov. 1, 1996.

TECHNICAL FIELD

The present invention relates to novel nucleoside derivatives having anti-viral activity, in particular, anti-HBV (anti-Hepatitis-B Virus) activity, represented by the following general formula (I):

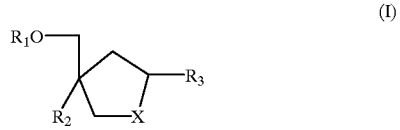

(I)

wherein $R_1$ represents hydrogen, phosphate, phosphonate, alkyl or acyl, $R_2$ represents alkoxy or halogen, $R_3$ represents substituted or non-substituted pyrimidine or purine base, and X represents O, S, SO or $SO_2$; pharmaceutically acceptable salts thereof, and processes for preparation thereof.

As a compound represented by general formula (I) has two or more asymmetric carbon atoms, the compound of the present invention represented by general formula (I) exists as a cis isomer as general formula (II) or trans isomer as general formula (III), or a mixture thereof.

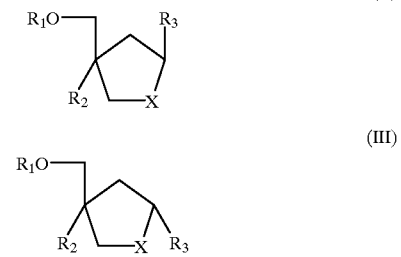

In the formula, $R_1$, $R_2$, $R_3$ and X are defined as above.

Each cis or trans isomer may exist as an optically pure isomer or as a mixture, i.e. racemic mixture. All isomers and mixture thereof mentioned above are included in the compounds of the present invention.

BACKGROUND ART

HBV is a lethal virus which causes acute or chronic viral hepatitis in human body and finally makes progress to liver cancer. Though the vaccines against the virus have been developed, a therapeutic agent has been hardly developed yet. Up to the present, Ara-A or interferon has been partially used for the treatment of hepatitis B, but both agents have many problems in their activity and safety.

Recently, a variety of nucleoside compounds having anti HBV activity have been reported.

For example, it is reported that 2',3'-dideoxy-3'-thiacytidine [Proc. Natl. Acad. Sci. USA, 88, 8495 (1991)], 5-fluoro-2',3'-dideoxy-3'-thiacytidine [Proc. Natl. Acad. Sci. USA, 88, 8495 (1991)], 2', 3'-dideoxy-β-L-5-fluorocytidine [Biochem. Pharm., 47, 171 (1994)], and 2', 3'-dideoxy-β-L-cytidine [Biochem. Pharm., 47, 171 (1994)] have anti-HBV activity.

However, these compounds leave much to be improved in view of their activity and safety, whereby development of novel compounds having more activity and less toxicity has still been required.

DICLOSURE OF THE INVENTION

The object of the present invention is to provide novel compounds having excellent anti-HBV activity with low toxicity, which are represented by general formula (I), and processes for preparation thereof.

In the compounds of the present invention, which are represented by general formula (I), $R_1$ represents hydrogen, phosphate, phosphonate, alkyl or acyl, $R_2$ represents alkoxy or halogen, $R_3$ represents pyrimidine or purine base which have natural origin, or their derivatives in which some portions of the base have been modified, and X represents O, S, SO or $SO_2$, as defined above.

Among the compounds represented by general formula (I), more preferable are the compounds in which $R_1$ represents hydrogen, phosphate or phosphonate, $R_2$ represents alkoxy or halogen, $R_3$ represents groups represented by the following formulas, and X represents O or S.

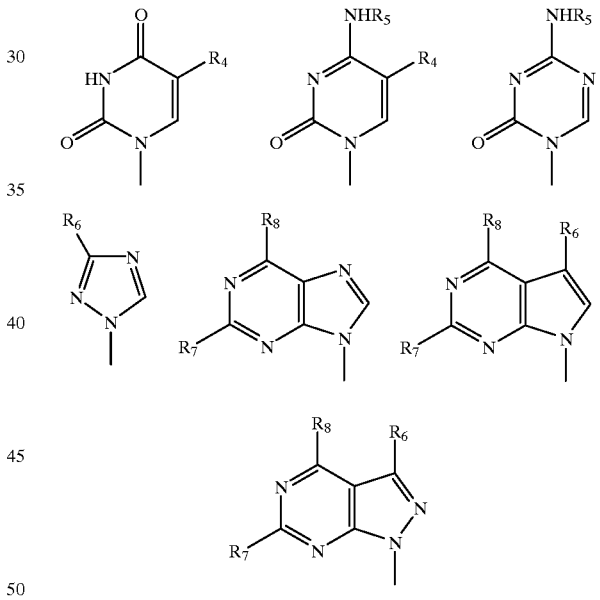

In the above formulas, $R_4$ represents hydrogen, saturated or unsaturated alkyl which may have (a) substituent(s), or halogen, $R_5$ represents hydrogen, hydroxy, alkoxy, saturated or unsaturated alkyl which may have (a) substituent(s), or saturated or unsaturated acyl which may have (a) substituent(s), $R_6$ represents hydrogen, cyano, carboxyl, alkoxycarbonyl, carbamoyl or thiocarbamoyl, and $R_7$ and $R_8$ each represents hydrogen, hydroxy, amino or halogen.

Among the compounds represented by general formula (I), the most preferable are the compounds in which $R_1$ represents hydrogen, phosphate or phosphonate, $R_2$ represents alkoxy or halogen, $R_3$ represents groups represented by the following formulas, and X represents O or S.

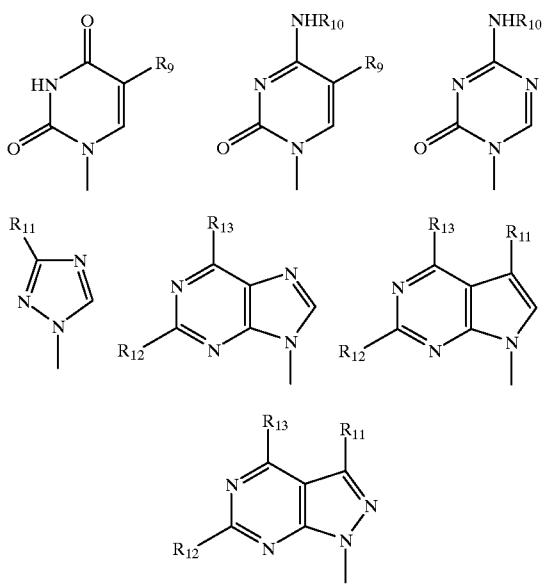

In the above formulas, $R_9$ represents hydrogen, methyl, hydroxymethyl, methoxymethyl, methylthiomethyl, trifluoromethyl, ethyl, propyl, cyclopropyl, vinyl, 2-bromovinyl, fluoro, chloro, bromo or iodo, $R_{10}$ represents hydrogen, methyl, ethyl, hydroxy, methoxy or $C_1$–$C_{16}$ acyl, $R_{11}$ represents hydrogen, cyano, carboxyl, alkoxycarbonyl, carbamoyl or thiocarbamoyl, and $R_{12}$ and $R_{13}$ each represents hydrogen, hydroxy, amino, fluoro, chloro, bromo or iodo.

The compound (I) of the present invention can be prepared by a conventional method which is well-known in the field of nucleic acid chemistry, as described below.

(Method A)

According to the most common method, the compound (I) can be obtained by reacting a five-membered ring represented by general formula (IV) with an appropriate base.

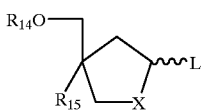

(IV)

In the above formula, $R_{14}$ represents hydrogen or protective group for hydroxy group, preferably alkyl, acyl or substituted silyl group, more preferably benzyl, acetyl, benzoyl, trimethylsilyl, tert-butyldimethylsilyl or tert-butyldiphenylsilyl group, $R_{15}$ represents alkoxy or halogen, X represents O, S, SO or $SO_2$, and L represents acyl, halide or alkoxy group, more preferably acetyl group.

More specifically, the compound (I) of the present invention can be obtained by a condensation reaction of compound (IV) with a base protected with a silyl group in the presence of a Lewis acid catalyst. As a desirable solvent for the reaction, mentioned are dichloromethane, 1,2-dichloroethane and acetonitrile. As a desirable Lewis acid catalyst, mentioned are tin chloride, titanium tetrachloride and silyl compounds such as trimethylsilyl triflate.

The compound of general formula (IV), which is used as a starting material for the preparation of compound (I) of the present invention, also is a novel compound. Among the compounds represented by general formula (IV), a compound wherein X is O can be prepared as shown in the following scheme I.

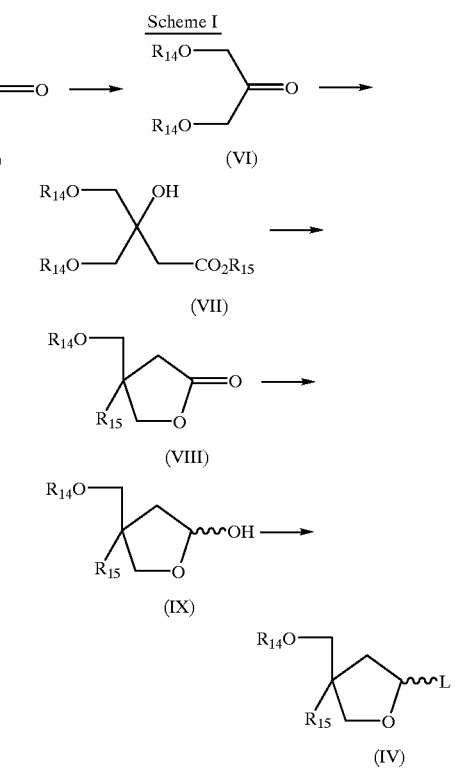

According to the scheme I, 1,3-dihydroxyacetone is reacted with a proper hydroxy protecting group to obtain compound (VI); the compound (VI) is reacted with alkyl bromoacetate and zinc (Reformatsky Reaction) or reacted with an enolate generated by treating alkyl acetate with a strong base such as LDA to obtain compound (VII); the compound (VII) is deprotected to obtain a lactone; the primary alcohol group is protected again with a proper protective group and then the tertiary alcohol group is properly halogenated to obtain the halide compound or alkylated to obtain the alkoxy compound (VIII); the compound (VIII) is reduced by a reducing agent such as diisobutyl aluminum hydride to obtain lactole (IX), and then the lactol is acylated, alkylated or halogenated to obtain the objective compound (IV). (In the above scheme I, $R_{14}$ of compound VI, VII, and VIII represents hydroxy protecting group.)

While another compound (IV) wherein X is S can be prepared as shown in the following scheme II.

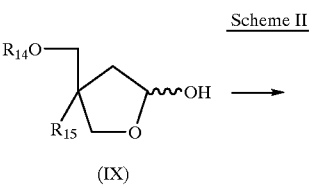

According to the scheme II, lactole (IX) is reacted with a benzylmercaptan to obtain intermediate (X); the intermediate (X) is reacted with triphenylphosphine and iodine to obtain tetrahydrothiophene derivatives (XI); the derivatives (XI) is reacted with LH in the presence of Lewis acid to obtain the objective compound (IV).

And also, the compound (IV) wherein X is SO, $SO_2$ can be prepared by oxidizing the compound (IV) wherein X is S with a proper oxidant.

(Method B)

A compound (I) may be converted to another compound (I) by substituting the base with other base.

The substitution process may be a chemical method (for instance, an uracil derivative is substituted with cytosine derivative), or a method using enzyme such as deoxyribose transferase. These base substitution processes are well known in the field of nucleic acid chemistry.

The compounds of general formula (I) prepared by the above processes are generally obtained as a mixture of cis and trans isomers.

The mixture can be separated by a physical method such as recrystallization or chromatography.

The compound of general formula (I) which is optically pure can be obtained by optical resolution of the racemic mixture or asymmetric synthesis starting from optically pure compound.

Pharmaceutically acceptable salts of the compound can be prepared by dissolving the compound in an appropriate solvent and reacting the compound with an acid or a base. Hydrochloric acid salt of the compound is most preferable.

This invention provides anti-HBV agent containing nucleoside derivatives represented by general formula (I). Hereby anti-HBV agent maybe administered for an adult in a daily dose of approximately 10 mg to 500 mg as nucleoside derivatives. Anti-HBV agent of the present invention may be administered in oral or non-oral dosage form.

BEST MODE FOR CARRYING OUT THE INVENTION

Here-in-after, the present invention will be described in detail by referring to the following Examples. However, it should be noted that the present invention is not restricted to these Examples.

EXAMPLE 1

4-(t-Butyldiphenylsilyloxymethyl)-4-hydroxytetrahydrofuran-2-one(1)

To a solution of 4-hydroxy-4-hydroxymethyltetrahydrofuran-2-one (7.8 g) in dry dichloromethane (200 ml), triethylamine (9.8 ml), t-butylchlorodiphenylsilane (16.9 ml) and 4-dimethylaminopyridine (360 mg) were added, and the resultant mixture was stirred at room temperature under nitrogen atmosphere for 10 hours. The reaction mixture was evaporated under reduced pressure, and the residue purified on a silica column (25% ethyl acetate/n-hexane) to give the title compound (20 g) as a white solid.

$^1$H NMR(CDCl$_3$) δ: 7.31–7.50(m, 10H), 4.12(s, 2H), 3.59(s, 2H), 2.48(s, 2H), 0.99(s, 9H),

EXAMPLE 2

4-(t-Butyldiphenylsilyloxymethyl)-4-fluorotetrahydrofuran-2-one(2)

A solution of diethylaminosulfur trifluoride (5 ml) in dry dichloromethane (100 ml) was cooled to −78° C., and a solution of 4-(t-butyldiphenylsilyloxymethyl)-4-hydroxytetrahydrofuran-2-one (14 g) in dry dichloromethane (100 ml) was added thereto. The reaction mixture was stirred at room temperature under nitrogen atmosphere for 1 hour. A cold aqueous solution (100 ml) of 10% sodium bicarbonate was added to the reaction mixture and the resultant mixture stirred for 30 minutes. The separated organic layer was dried over anhydrous magnesium sulfate, filtered and concentrated under reduced pressure.

The residue was purified on a silica column (10% ethyl acetate/n-hexane) to obtain the objective compound (2.5 g) as a pale yellow liquid.

$^1$H NMR (CDCl$_3$) δ: 7.25–7.65(m, 10H), 4.51(s, 1H), 4.38(d, 1H), 3.86(s, 1H), 3.79(d, 1H), 2.86(dd, 1H), 2.73(dd, 1H), 1.07(s, 9H)

EXAMPLE 3

4-(t-Butyldiphenylsilyloxymethyl)-4-fluorotetrahydrofuran-2-ol(3)

A solution of 4-(t-butyldiphenylsilyloxymethyl)-4-fluorotetrahydrofuran-2-one (2.59 g) in dry dichloromethane (50 ml) was cooled to −78° C., and 1.0 M solution (7 ml) of diisobutyl aluminum hydride was added thereto.

After stirring the reaction mixture at −78° C. under nitrogen atmosphere for 30 minutes, a saturated aqueous solution (20 ml) of potassium sodium tartrate was added thereto, and the mixture stirred at room temperature for 3 hours. The separated organic layer was dried over anhydrous magnesium sulfate, filtered and concentrated under reduced pressure. Thus obtained yellow liquid was used in the following step without further purification.

EXAMPLE 4

4-(t-Butyldiphenylsilyloxymethyl)-2-acetoxy-4-fluorotetrahydrofuran(4)

4-(t-Butyldiphenylsilyloxymethyl)-4-fluorotetrahydrofuran-2-ol obtained in Example 3 was dissolved in dry dichloromethane (50 ml), and triethylamine (1.1 ml), acetic anhydride (0.7 ml) and 4-dimethylaminopyridine (42 mg) were added thereto.

After stirring the reaction mixture at room temperature for 30 minutes, water (10 ml) was added and the mixture stirred for 10 minutes. The separated organic layer was dried over anhydrous magnesium sulfate, filtered and concentrated under reduced pressure.

The residue was purified on a silica colomn (10% ethyl acetate/n-hexane) to obtain the objective compound (2 g) as white solid.

$^1$H NMR (CDCl$_3$) δ: 7.39–7.67(m, 10H), 6.45(dd, 1H), 4.08–4.29(m, 2H), 3.78–3.94(m, 2H), 2.27–2.61(m, 2H), 2.02(s, 3H), 1.07(s, 9H)

EXAMPLE 5 cis-2-(Thymin-1-yl)-4-fluoro-4-hydroxymethyltetrahydrofuran(5) and trans-2-(Thymin-1-yl)-4-fluoro-4-hydroxymethyltetrahydrofuran(6)

Thymine (303 mg) was suspended in 1,1,1,3,3,3-hexamethyldisilazane (20 ml), and ammonium sulfate (catalytic amount) was added thereto. The mixture was heated under reflux with stirring under nitrogen atmosphere for 4 hours. Then, the mixture was evaporated under reduced pressure to remove 1,1,1,3,3,3-hexamethyldisilazane. To the residue, dry 1,2-dichloroethane (20 ml) was added and then a solution of 4-(t-butyldiphenylsilyloxymethyl)-2-acetoxy-4-fluorotetrahydrofuran (500 mg) in dry 1,2-dichloroethane (10 ml) was added thereto.

After cooling the reaction mixture to 0° C., trimethylsilyltrifluoromethanesulfonate (0.47 ml) was added dropwise, and the mixture stirred at 0° C. under nitrogen atmosphere for 30 minutes. Saturated aqueous solution (20 ml) of sodium bicarbonate was added thereto, and the resultant mixture was stirred at room temperature for 30 minutes. Insoluble materials were removed by filtration, and the organic layer separated from the filtrate was dried over anhydrous magnesium sulfate, filtered and concentrated under reduced pressure. The residue was purified on a silica column (50% ethyl acetate/n-hexane) to obtain the title compounds, cis-isomer (135 mg) and trans-isomer (75 mg), respectively as white solid.

Each of the obtained isomers was dissolved in THF (15 ml), and 1.0 M solution of tetrabutylammonium fluoride was added to the solution. The resultant mixture was stirred at room temperature for 1 hour and concentrated under reduced pressure. The residue was purified on a silica column (5% methanol/dichloromethane) to obtain the objective compounds, cis-isomer (64 mg) and trans-isomer (35 mg), as white solid.

trans-isomer $^1$H NMR (DMSO-d$_6$) δ: 11.29(br. s, 1H), 7.38(s, 1H), 6.07(dd, 1H), 5.27(t, 1H), 4.30–4.22(m, 1H), 3.95–3.83(m, 1H), 3.68–3.59(m, 2H), 2.64–2.48(m, 1H), 2.22–2.17(m, 1H), 1.77(s, 3H)

UV (H$_2$O) λ$_{max}$: 267.4 nm(pH 7), 267.2 nm(pH 2), 265.4 nm(pH 11)

cis-isomer $^1$H NMR (DMSO-d$_6$) δ: 11.30(s, 1H), 7.55(d, 1H), 6.13(t, 1H), 5.25(t, 1H), 4.26–4.15(m, 1H), 3.97–3.89(m, 1H), 6.3.73–3.65(m, 2H), 2.43–2.26(m, 2H), 1.77(s, 3H)

UV (H$_2$O) λ$_{max}$: 265.8 nm(pH 7), 266.0 nm(pH 2), 265.8 nm(pH 11)

EXAMPLE 6 cis-2-(Cytosin-1-yl)-4-fluoro-4-hydroxymethyltetrahydrofuran(7) and trans-2-(Cytosin-1-yl)-4-fluoro-4-hydroxymethyltetrahydrofuran(8)

N$^4$-Acetylcytosine (368 mg) was suspended in 1,1,1,3,3,3-hexamethyldisilazane (20 ml), and ammonium sulfate (catalytic amount) was added thereto. The mixture was heated under refulx with stirring under nitrogen atmosphere for 4 hours. Then, the mixture was evaporated under reduced pressure to remove 1,1,1,3,3,3-hexamethyldisilazane. To the residue, dry 1,2-dichloroethane (15 ml) was added to dissolve the residue. Then, a solution of 4-(t-butyldiphenylsilyloxymethyl)-2-acetoxy-4-fluorotetrahydrofuran (500 mg) in dry 1,2-dichloroethane (10 ml) was added thereto.

After cooling the reaction mixture to −10° C., trimethylsilyltrifluoromethanesulfonate (0.47 ml) was added dropwise, and the mixture stirred at −10° C. under nitrogen atmosphere for 20 minutes. Saturated aqueous solution (20 ml) of sodium bicarbonate was added thereto, and the resultant mixture stirred at room temperature for 10 minutes. Insoluble materials were removed by filtration, and the organic layer separated from the filtrate was dried over anhydrous magnesium sulfate, filtered and concentrated under reduced pressure. The residue was purified on a silica column (ethyl acetate/n-hexane) to obtain the title compounds, cis-isomer (158 mg) and trans-isomer (157 mg), respectively as white solid. To the obtained white solid, saturated methanolic ammonia solution (7 ml) was added. The mixture stirred under nitrogen atmosphere for 30 minutes and concentrated under reduced pressure.

Each of the obtained isomers was dissolved in THF (15 ml), and 1.0 M solution of tetrabutylammonium fluoride was added to the solution. The resultant mixture was stirred at room temperature for 1 hour and concentrated under reduced pressure. The residue was purified on a silica column (10% methanol/dichloromethane) to obtain the objective compounds, cis-isomer (51 mg) and trans-isomer (64 mg), as white solid.

trans-isomer $^1$H NMR (DMSO-d$_6$) δ: 7.53(d, 1H), 7.12–7.03(br.d, 2H), 6.02(dd. 1H), 5.71(d, 1H), 5.24(t, 1H), 4.26–4.21(m,1H), 4.00–3.88(m, 1H), 3.66–3.57(m, 2H), 2.59–2.52(m, 1H), 2.12–2.07(m, 1H)

UV (H$_2$O) λ$_{max}$: 269.8, 229.2 (sh) nm (pH 7), 278.6, 219.6 (sh) nm (pH 2), 270.2 nm(pH 11)

cis-isomer $^1$H NMR (DMSO-d$_6$) δ: 7.60(d, 1H), 7.16–7.12(br.d, 2H), 6.10(t, 1H), 5.70(d, 1H), 5.23(t, 1H), 4.24–4.13(m, 1H), 3.98–3.89(m, 1H), 3.70–3.62(m, 2H), 2.45–2.38(m, 1H), 2.26–2.15(m, 1H)

UV (H$_2$O) λ$_{max}$: 269.4, 229.0 (sh) nm(pH 7), 278.0, 209.0 (sh) nm (pH 2), 269.8 nm (pH 11)

EXAMPLE 7 cis-2-(5-Fluorocytosin-1-yl)-4-fluoro-4-hydroxymethyltetrahydrofuran(9) and trans-2-(5-Fluorocytosin-1-yl)-4-fluoro-4-hydroxymethyltetrahydrofuran(10)

N$^4$-Acetyl-5-fluorocytosine (621 mg) was suspended in 1,1,1,3,3,3-hexamethyldisilazane (16 ml), and ammonium sulfate (catalytic amount) was added thereto. The mixture was heated under reflux with stirring under nitrogen atmosphere for 4 hours. Then, the mixture was evaporated under reduced pressure to remove 1,1,1,3,3,3-hexamethyldisilazane. To the residue, dry 1,2-dichloroethane (15 ml) was added to dissolve the residue. Then, a solution of 4-(t-butyldiphenylsilyloxymethyl)-2-acetoxy-4-fluorotetrahydrofuran (500 mg) in dry 1,2-dichloroethane (10 ml) was added thereto.

After cooling the reaction mixture to 0° C., trimethylsilyltrifluoromethanesulfonate (0.47 ml) was added dropwise, and the mixture was stirred at 0° C. under nitrogen atmosphere for 20 minutes. Saturated aqueous solution (20 ml) of sodium bicarbonate was added thereto, and the resultant mixture stirred at room temperature for 30 minutes. Insoluble materials were removed by filtration, and the organic layer separated from the filtrate was dried over anhydrous magnesium sulfate, filtered and concentrated under reduced pressure. The residue was purified on a silica column (20% ethyl acetate/n-hexane) to obtain the title compounds, cis-isomer (321 mg) and trans-isomer (220 mg), respectively as white solid. To the obtained white solid, saturated methanolic ammonia solution (7 ml) was added. The mixture stirred under nitrogen atmosphere for 6 hours and concentrated under reduced pressure.

Each of the obtained isomers was dissolved in THF (15 ml), and 1.0 M solution of tetrabutylammonium fluoride was added to the solution. The resultant mixture was stirred at room temperature for 1 hour and concentrated under reduced pressure. The residue was purified on a silica column (7% methanol/chloroform) to obtain the objective compounds, cis-isomer (95 mg) and trans-isomer (115 mg), as white solid.

trans-isomer $^1$H NMR (DMSO-d$_6$) δ: 7.68(br.d, 1H), 7.50(br.s, 1H), 5.97(d, 1H), 5.25(t, 1H), 4.35–4.30(m, 1H), 4.00–3.88(m, 1H), 3.66–3.57(m, 2H), 2.65–2.60(m, 1H), 2.19–2.14(m, 1H)

UV (H$_2$O) λ$_{max}$: 279.4, 232.6 (sh) mn(pH 7), 288.6, 212.4 (sh) mn(pH 2), 278.4 nm(pH 11)

cis-isomer $^1$H NMR (DMSO-d$_6$) δ: 7.92(d, 1H), 7.85–7.12 (br.s, 1H), 7.65(br.s, 1H), 6.08(t, 1H), 5.22(t, 1H), 4.28–4.16 (m, 1H), 3.95–3.85(m, 1H), 3.70–3.64(m, 2H), 2.47–2.43 (m, 1H), 2.27–2.15(m, 1H)

UV (H$_2$O) λ$_{max}$: 279.6, 236.2 (sh) nm (pH 7), 286.2, 211.6 (sh) nm (pH 2), 279.2 nm (pH 11)

EXAMPLE 8 cis-2-(5Fluorouracil-1-yl)-4-fluoro-4-hydroxymethyltetrahydrofuran(11) and trans-2-(5-Fluorouracil-1-yl)-4-fluoro-4-hydroxymethyltetrahydrofuran(12)

5-Fluorouracil (310 mg) was suspended in 1,1,1,3,3,3-hexamethyldisilazane (15 ml), and ammonium sulfate (catalytic amount) was added thereto. The mixture was heated under refulx with stirring under nitrogen atmosphere for 8 hours. Then, the mixture was evaporated under reduced pressure to remove 1,1,1,3,3,3-hexamethyldisilazane. To the residue, dry 1,2-dichloroethane (20 ml) was added. Then, a solution of 4-(t-butyldiphenylsilyloxymethyl)-2-acetoxy-4-fluorotetrahydrofuran (500 mg) in dry 1,2-dichloroethane (10 ml) was added thereto.

After cooling the reaction mixture to 0° C., trimethylsilyltrifluoromethanesulfonate (0.47 ml) was added dropwise, and the mixture stirred at 0° C. under nitrogen atmosphere for 20 minutes. Saturated aqueous solution (20 ml) of sodium bicarbonate was added thereto, and the resultant mixture stirred at room temperature for 30 minutes. Insoluble materials were removed by filtration, and the organic layer separated from the filtrate was dried over anhydrous magnesium sulfate, filtered and concentrated under reduced pressure. The residue was purified on a silica column (33% ethyl acetate/n-hexane) to obtain the title compounds, cis-isomer (182 mg) and trans-isomer (268 mg), respectively as white solid.

Each of the obtained isomers was dissolved in THF (7 ml), and 1.0 M solution of tetrabutylammonium fluoride was added to the solution. The resultant mixture was stirred at room temperature for 1 hour and concentrated under reduced pressure. The residue was purified on a silica column (66% ethyl acetate/n-hexane) to obtain the objective compounds, cis-isomer (74 mg) and trans-isomer (127 mg), as white solid.

trans-isomer $^1$H NMR (DMSO-d$_6$) δ: 11.83(br.s, 1H), 7.75(d, 1H), 6.04(d.d, 1H), 5.28(t, 1H), 4.38–4.30(m, 1H), 3.98–3.89(m, 1H), 3.67–3.59(m, 2H), 2.63–2.52(m, 1H), 2.30–2.15(m, 1H)

UV (H$_2$O) λ$_{max}$: 268.6 nm(pH 7), 268.6 nm(pH2), 268.4 mn(pH 11)

cis-isomer $^1$H NMR (DMSO-d$_6$) δ: 11.8(br.s, 1H), 8.07(d, 1H), 6,11(t, 1H), 5.25(t, 1H), 4.28–4.16(m, 1H), 3.98–3.90(m, 1H), 3.73–3.65(m, 2H), 2.48–2.28(m, 2H)

UV (H$_2$O) λ$_{max}$: 268.2 nm(pH 7), 268.2 nm(pH2), 268.0 nm(pH 11)

EXAMPLE 9 cis-2-(5-Chlorouracil-1-yl)-4-fluoro-4-hydroxymethyltetrahydrofuran(13) and trans-2-(5-chlorouracil-1-yl)-4-fluoro-4-hydroxymethyltetrahydrofuran(14)

5-Chlorouracil (312 mg) was suspended in 1,1,1,3,3,3-hexamethyldisilazane (15 ml), and ammonium sulfate (catalytic amount) was added thereto. The mixture was heated under refulx with stirring under nitrogen atmosphere for 3.5 hours. Then, the mixture was evaporated under reduced pressure to remove 1,1,1,3,3,3-hexamethyldisilazane. To the residue, dry 1,2-dichloroethane (20 ml) was added. Then, a solution of 4-(t-butyldiphenylsilyloxymethyl)-2-acetoxy-4-fluorotetrahydrofuran (500 mg) in dry 1,2-dichloroethane (10 ml) was added thereto.

After cooling the reaction mixture to 0° C., trimethylsilyltrifluoromethanesulfonate (0.47 ml) was added dropwise, and the mixture stirred at 0° C. under nitrogen atmosphere for 20 minutes. Saturated aqueous solution (20 ml) of sodium bicarbonate was added thereto, and the resultant mixture stirred at room temperature for 30 minutes. Insoluble materials were removed by filtration, and the organic layer separated from the filtrate was dried over anhydrous magnesium sulfate, filtered and concentrated under reduced pressure. The residue was purified on a silica column (50% ethyl acetate/n-hexane) to obtain the title compounds, cis-isomer (73 mg) and trans-isomer (340 mg), respectively as white solid.

Each of the obtained isomers was dissolved in THF (7 ml), and 1.0 M solution of tetrabutylammonium fluoride was added to the solution. The resultant mixture was stirred at room temperature for 1 hour and concentrated under reduced pressure. The residue was purified on a silica column (66% ethyl acetate/n-hexane) to obtain the objective compounds, cis-isomer (30 mg) and trans-isomer (110 mg), as white solid.

trans-isomer $^1$H NMR (DMSO-d$_6$) δ: 11.86(br.s, 1H), 7.78(s, 1H), 6.05(dd, 1H), 5.28(t, 1H), 4.40–4.32(m, 1H), 3.99–3.87(m, 1H), 3.68–3.59(m, 2H), 2.64–2.53(m, 1H), 2.33–2.27(m, 1H)

UV (H$_2$O) λ max: 276.2 nm(pH 7), 276.4 nm(pH 2), 274.2 nm(pH 11)

cis-isomer $^1$H NMR (DMSO-d$_6$) δ: 11.85(br.s, 1H), 8.12(s, 1H), 6.09(t, 1H), 5.25(t, 1H), 4.30–4.18(m, 1H), 4.02–3.93(m, 1H), 3.73–3.65(m, 2H), 2.45–2.41(m, 2H)

UV (H$_2$O) λ max: 275.6 nm(pH 7), 275.8 nm(pH 2), 273.8 nm(pH 11)

EXAMPLE 10 cis-2-(5-Iodouracil-1-yl)-4-fluoro-4-hydroxymethyltetrahydrofuran(15) and trans-2-(5-iodouracil-1-yl)-4-fluoro-4-hydroxymethyltetrahydrofuran(16)

5-Iodouracil (571 mg) was suspended in 1,1,1,3,3,3-hexamethyldisilazane (20 ml), and ammonium sulfate (catalytic amount) was added thereto. The mixture was heated under reflux with stirring under nitrogen atmosphere for 2 hours. Then, the mixture was evaporated under reduced pressure to remove 1,1,1,3,3,3-hexamethyldisilazane. To the residue, dry 1,2-dichloroethane (20 ml) was added. Then, a solution of 4-(t-butyldiphenylsilyloxymethyl)-2-acetoxy-4-fluorotetrahydrofuran (500 mg) in dry 1,2-dichloroethane (10 ml) was added thereto.

After cooling the reaction mixture to 0° C., trimethylsilyltrifluoromethanesulfonate (0.47 ml) was added dropwise, and the mixture stirred at 0° C. under nitrogen atmosphere for 20 minutes. Saturated aqueous solution (20 ml) of sodium bicarbonate was added thereto, and the resultant mixture stirred at room temperature for 30 minutes. Insoluble materials were removed by filtration, and the organic layer separated from the filtrate was dried over anhydrous magnesium sulfate, filtered and concentrated under reduced pressure. The residue was purified on a silica column (33% ethyl acetate/n-hexane) to obtain the title compounds, cis-isomer (248 mg) and trans-isomer (325 mg), respectively as white solid.

Each of the obtained isomers was dissolved in THF (7 ml), and 1.0 M solution of tetrabutylammonium fluoride was added to the solution. The resultant mixture was stirred at room temperature for 1 hour and concentrated under reduced pressure. The residue was purified on a silica column (7% methanol/chloroform) to obtain the objective compounds, cis-isomer (99 mg) and trans-isomer (149 mg), as white solid.

trans-isomer
$^1$H NMR (DMSO-d$_6$) δ: 11.69(br.s, 1H), 7.86(s, 1H), 6.06(dd, 1H), 5.28(br.s, 1H), 2.37–2.24(m, 1H), 3.97–3.88 (m, 1H), 3.67–3.63(m, 2H), 2.64–2.45(m, 1H), 2.29–2.20 (m, 1H)
UV (H$_2$O) λ$_{max}$: 285.2 nm(pH 7), 286.4 nm(pH 2), 276.8 nm(pH 11)

cis-isomer
$^1$H NMR (DMSO-d$_6$) δ: 11.69(br.s, 1H), 8.15(s, 1H), 6.08(t, 1H), 4.25–4.17(m, 1H), 3.97–3.86(m, 1H), 3.72–3.67 (m, 2H), 2.49–2.42(m, 2H)
UV (H$_2$O) λ$_{max}$: 286.8 mn(pH 7), 286.2 nm(pH 2), 278.2 nm(pH 11)

EXAMPLE 11

2-(Guanin-9-yl)-4-fluoro-4-hydroxymethyltetrahydrofuran(17)

N$^2$-Acetyl-O$^6$-diphenylcarbamoylguanine (355 mg) was suspended in dry 1,2-dichloroethane (15 ml), and N,O-bis(trimethylsilyl)acetamide (0.61 ml) was added thereto. The mixture was then heated under refulx with stirring under nitrogen atmosphere for 1 hour.

After cooling the reaction mixture to room temperature, a solution of 4-(t-butyldiphenylsilyloxymethyl)-2-acetoxy-4-fluorotetrahydrofuran (290 mg) in dry 1,2-dichloroethane (5 ml) was added thereto. After chilling the reaction mixture to 0° C., trimethylsilyltrifluoromethane sulfonate (0.2 ml) was added dropwise, and the mixture stirred under nitrogen atmosphere for 1 hour. Saturated aqueous solution (10 ml) of sodium bicarbonate was added and the mixture stirred for 10 minutes. Separated organic layer was dried over anhydrous magnesium sulfate, filtered and concentrated under reduced pressure. To the residue, saturated methanolic ammonia solution (10 ml) was added, and the mixture stirred at room temperature for 20 hours.

To the residue obtained after concentrating the mixture, THF (5 ml) was added, and then 1.0 M solution (0.5 ml) of tetrabutylammonium fluoride was added. The mixture was stirred at room temperature for 2 hours. After concentrating under reduced pressure, the residue was purified on a silica column (10% methanol/dichloromethane) to obtain the title compound (65 mg) as pale yellow solid.

$^1$H NMR (DMSO-d$_6$) δ: 10.80(bs, 1H), 7.98, 7.88(s each, 1H), 6.61(br, 2H), 6.05–6.25(m, 1H), 5.33(bs, 1H), 3.60–4.31(m, 4H), 2.50–2.81(m, 2H)

UV (H$_2$O) λ$_{max}$: 252, 271(sh) nm(pH 7), 254, 270(sh) mn(pH 2), 266 mn (pH 11)

EXAMPLE 12

4-(t-Butyldiphenylsilyloxymethyl)-4-fluoro-2-(6-chloropurin-9-yl)tetrahydrofuran(18)

6-Chloropurine (150 mg) was suspended in 1,1,1,3,3,3-hexamethyldisilazane (15 ml), and ammonium sulfate (catalytic amount) and chlorotrimethylsilane (catalytic amount) were added thereto. The mixture was heated under reflux with stirring under nitrogen atmosphere for 4 hours. 1,1,1,3,3,3-hexamethyldisilazane was removed by evaporating under reduced pressure, and then dry 1,2-dichloroethane (10 ml) was added to the residue. Then, a solution of 4-(t-butyldiphenylsilyloxymethyl)-2-acetoxy-4-fluorotetrahydrofuran (200 mg) in dry 1,2-dichloroethane (5 ml) was added thereto.

After cooling the reaction mixture at 0° C., trimethylsilyltrifluoromethanesulfonate (0.19 ml) was added dropwise, and the resultant mixture was stirred at 0° C. under nitrogen atmosphere for 20 minutes. Saturated aqueous solution (10 ml) of sodium bicarbonate was added to the reaction mixture, and the mixture stirred at room temperature for 10 minutes. Insoluble materials were filtered off, and the organic layer separated from the filtrate was dried over anhydrous magnesium sulfate, filtered and concentrated under reduced pressure. The residue was purified on a silica column (20% ethyl acetate/n-hexane) to obtain the title compound (120 mg) as colorless caramel-like material.

EXAMPLE 13

2-(6-Chloropurine-9-yl)-4-fluoro-4-hydroxymethyltetrahydrofuran(19)

To a solution of 4-(t-butyldiphenylsilyloxymethyl)-4-fluoro-2-(6-chloropurin-9-yl)tetrahydrofuran (100 mg) in tetrahydrofuran (5 ml), 1.0 M solution (0.2 ml) of tetrabutylammonium fluoride was added, and the mixture stirred at room temperature for 2 hours. After concentrating under reduced pressure, the residue was purified on a silica column (6% methanol/dichloromethane) to obtain the title compound (30 mg) as colorless caramel-like material.

¹H NMR (DMSO-d₆) δ: 9.00(s, 1H), 8.94(s, 1H), 6.75(t, 1H), 5.25(t, 1H), 4.20–4.54(m, 2H), 3.82–4.00(m, 2H), 2.88–3.21(m, 2H)

UV (H₂O) $\lambda_{max}$: 264.5nm (pH 7.2 및 11)

EXAMPLE 14 cis-2-(3-Carbamoyl-1,2,4-triazol-1-yl)-4-fluoro-4-hydroxymethyltetrahydrofuran(20) and trans-2-(3-carbamoyl-1,2,4-triazol-1-yl)-4-fluoro-4-hydroxymethyltetrahydrofuran(21)

1,2,4-Triazol-3-carboxylatemethylester (304 mg) was suspended in dry 1,2-dichloroethane (15 ml), and N,O-bis(trimethylsilyl)acetamide (0.61 ml) was added thereto. The mixture was then heated under reflux with stirring under nitrogen atmosphere for 4 hours. Then, the mixture was evaporated under reduced pressure to remove 1,1,1,3,3,3-hexamethyldisilazane. To the residue, dry 1,2-dichloroethane (15 ml) was added. Then, a solution of 4-(t-butyldiphenylsilyloxymethyl)-2-acetoxy-4-fluorotetrahydrofuran (500 mg) in dry 1,2-dichloroethane (10 ml) was added thereto.

After cooling the reaction mixture to 0° C., trimethylsilyltrifluoromethanesulfonate (0.47 ml) was added dropwise. The mixture stirred at 0° C. under nitrogen atmosphere for 30 minutes and then stirred overnight at room temperature. Saturated aqueous solution (20 ml) of sodium bicarbonate was added thereto, and the resultant mixture stirred at room temperature for 30 minutes. Insoluble materials were removed by filtration, and the organic layer separated from the filtrate was dried over anhydrous magnesium sulfate, filtered and concentrated under reduced pressure. The residue was purified on a silica column (60% ethyl acetate/n-hexane) to obtain the pale yellow oil (350 mg).

The obtained oil was dissolved in THF (15 ml), and 1.0 M solution of tetrabutylammonium fluoride (0.89 ml) was added to the solution. The resultant mixture was stirred at room temperature for 2 hour and concentrated under reduced pressure. The residue was purified on a silica column (33% ethyl acetate/n-hexane) to obtain cis-isomer (60 mg) and trans-isomer (24.9 mg) respectively as the colorless oil.

To the obtained colorless oil, saturated methanolic ammonia solution (7 ml) was added. The mixture stirred under nitrogen atmosphere overnight and concentrated under reduced pressure.

The residue was purified on a silica column (5% methanol/ethyl acetate) to obtain the objective compounds, cis-isomer (33 mg) and trans-isomer (11 mg) as white solid.

trans-isomer

¹H NMR (DMSO-d₆) δ: 8.69(s, 1H), 7.79(br.s, 1H), 7.58(br.s, 1H), 6.26(dd, 1H), 5.36(br.s, 2H), 4.28–4.05(m, 2H), 3.67–3.61(m, 1H), 2.74–2.48(m, 2H)

cis-isoimer

¹H NMR (DMSO-d₆) δ: 8.80(s, 1H), 7.83(br.s, 1H), 7.62(br.s, 1H), 6.46(t, 1H), 5.33(t, 1H), 4.16–4.03(m, 2H), 3.81–3.71(m, 2H), 2.78–2.68(m, 2H)

EXAMPLE 15

4-(t-Butyldiphenylsilyloxymethyl)-4-methoxytetrahydrofuran-2-one(22)

To a solution of 4-(t-butyldiphenylsilyloxymethyl)-4-hydroxytetrahydrofuran-2-one (3 g) in iodomethane (10 ml), silver oxide (11.3 g) was added, and the mixture stirred at room temperature for 3 days. After filterred and concentrated under reduced pressure, the residue was purified on a silica column (25% ethyl acetate/n-hexane) to obtain the objective compound(1.9 g) as yellow solution.

¹H NMR (DMSO-d₆) δ: 7.61–7.64(m, 4H), 7.39–7.47(m, 6H), 4.36(d, 1H), 4.29(d, 1H), 3.71(s, 2H), 3.23(s, 3H), 2.77(d, 1H), 2.60(d, 1H), 1.08(s, 9H)

EXAMPLE 16

4-(t-Butyldiphenylsilyloxymethyl)-4-methoxytetrahydrofuran-2-ol(23)

After cooling a solution of 4-(t-butyldiphenylsilyloxymethyl)-4-methoxytetrahydrofuran-2-one, obtained in example 15, in dry dichloromethane (10 ml) to −78° C., the solution of 1.0 M diisobutylaluminium hydride (6 ml) was added dropwise. The mixture stirred at −78° C. under nitrogen atmosphere for 10 minutes and then stirred overnight at room temperature. Saturated aqueous solution (10 ml) of potassium sodium tartrate was added thereto, and the resultant mixture stirred at room temperature for 20 hours. The organic layer separated from the filtrate was dried over anhydrous magnesium sulfate, filtered and concentrated under reduced pressure. The obtained yellowish solution was used in the following step without further purification.

EXAMPLE 17

2-Acetoxy 4-(t-butyldiphenylsilyloxymethyl)-4-methoxytetrahydrofuran(24)

To the solution of 4-(t-butyldiphenylsilyloxymethyl)-4-methoxytetrahydrofuran-2-ol, obtained in example 16, in dry dichloromethane (5 ml), triethylamine (0.85 ml), acetic anhydride (0.6 ml) and 4-diethylaminopyridine (40 ml) were added dropwise. The resultant mixture was stirred at room temperature for 12 hours and concentrated under reduced pressure. The residue was purified on a silica column (100% ethyl acetate/n-hexane) to obtain the objective compound (1.2 g) as the yellowish solution.

¹H NMR (CDCl₃) δ: 7.64–7.68(m, 4H), 7.38–7.47(m, 6H), 6.40(dd, 0.64H), 6.23(dd, 0.36H), 4.08(d, 0.36H), 4.03(d, 0.26H), 4.02(s, 1.28H), 3.80(d, 0.69H), 3.74(d, 0.64H), 3.70(s, 0.72H), 3.01(s, 1.08H), 3.25(s, 1.92H), 2.38 (dd, 0.72H), 2.15–2.30(m, 1.28H), 2.08(s, 1.08H), 1.99(s, 1.92H), 1.09(s, 5.76H), 1.08(s, 3.24H)

EXAMPLE 18 cis-2-(Thymin-1-yl)-4-methoxy-4-hydroxymethyltetrahydrofuran (25) and trans-2-(thymin-1-yl)-4-methoxy-4-hydroxymethyltetrahydrofuran(26)

Thymine (155 mg) was suspended in 1,1,1,3,3,3-hexamethyldisilazane (15 ml), and ammonium sulfate (catalytic amount) was added thereto. The mixture was heated under reflux with stirring under nitrogen atmosphere for 5 hours. Then, the mixture was evaporated under reduced pressure to remove 1,1,1,3,3,3-hexamethyldisilazane. To the residue, dry 1,2-dichloroethane (20 ml) was added. Then, a solution of 2-acetoxy-4-(t-butyldiphenylsilyloxymethyl)4-methoxytetrahydrofuran (263 mg) in dry 1,2-dichloroethane (5 ml) was added thereto.

After cooling the reaction mixture to 0° C., trimethylsilyltrifluoromethanesulfonate (0.24 ml) was added dropwise, and the mixture stirred at 0° C. under nitrogen atmosphere for 10 minutes. Saturated aqueous solution (10 ml) of sodium bicarbonate was added thereto, and the resultant mixture stirred at room temperature for 30 minutes. Insoluble materials were removed by filtration, and the organic layer separated from the filtrate was dried over anhydrous magnesium sulfate, filtered and concentrated under reduced pressure. The residue was purified on a silica column (ethyl acetate), recrystallized with dichloroethane/n-hexane (1:1) to obtain cis-isomer (35 mg) and trans-isomer (69 mg), respectively as pale yellow solid.

Each of the obtained isomers was dissolved in THF (1 ml), and 1.0 M solution of tetrabutylammonium fluoride was added to the solution. The resultant mixture was stirred at room temperature for 2 hours and concentrated under reduced pressure. The residue was purified on a silica column (ethyl acetate) to obtain the objective compounds, cis-isomer (11.2 mg) and trans-isomer (19.6 mg), as pale yellow solid.

trans-isomer $^1$H NMR (DMSO-$d_6$) δ: 11.23(br.s, 1H), 7.52(d, 1H), 6.01(dd, 1H), 4.93(t, 1H), 4.09(dd, 1H), 3.72(d, 1H), 3.57–3.49(m, 2H), 3.15(s, 3H), 2.33–2.28(m, 1H), 2.09–2.05(m, 1H), 1.77(s, 3H)

cis-isomer $^1$H NMR (DMSO-$d_6$) δ: 11.25(br.s, 1H), 7.52(d, 1H), 6.06(t, 1H), 4.92(t, 1H), 4.02(d, 1H), 3.83(d, 1H), 3.64–3.53 (m, 2H), 3.22(s, 3H), 2.34–2.29(m, 1H), 1.99–1.95(m, 1H), 1.77(s, 3H)

UV($H_2O$) $\lambda_{max}$: 268 nm(pH 7), 267 nm(pH 2), 266.7 nm(pH 11)

EXAMPLE 19

(cis, trans)-2-(Cytosin-1-yl)-4-methoxy-4-hydroxymethyltetrahydrofuran(27)

$N^4$-Acetylcytosine (306 mg) was suspended in 1,1,1,3,3,3-hexamethyldisilazane (20 ml), and ammonium sulfate (catalytic amount) was added thereto. The mixture was heated under refulx with stirring under nitrogen atmosphere for 4 hours. Then, the mixture was evaporated under reduced pressure to remove 1,1,1,3,3,3-hexamethyldisilazane. To the residue, dry 1,2-dichloroethane (15 ml) was added to dissolve the residue. Then, a solution of 4-(t-butyldiphenylsilyloxymethyl)-2-acetoxy-4-fluorotetrahydrofuran (261 mg) in dry 1,2-dichloroethane (10 ml) was added thereto.

After cooling the reaction mixture to −10° C., trimethylsilyltrifluoromethanesulfonate (0.23 ml) was added dropwise, and the mixture stirred at −10° C. under nitrogen atmosphere for 20 minutes. Saturated aqueous solution (25 ml) of sodium bicarbonate was added thereto, and the resultant mixture stirred at room temperature for 10 minutes. Insoluble materials were removed by filtration, and the organic layer separated from the filtrate was dried over anhydrous magnesium sulfate, filtered and concentrated under reduced pressure. To the obtained the pale yellow solution, saturated methanolic ammonia solution (7 ml) was added. The mixture stirred under nitrogen atmosphere for 30 minutes and concentrated under reduced pressure.

Each of the obtained isomers was dissolved in THF (15 ml), and 1.0 M solution of tetrabutylammonium fluoride was added to the solution. The resultant mixture was stirred at room temperature for 1 hour and concentrated under reduced pressure. The residue was purified on a silica column (10% methanol/chloroform) and recrystallized to obtain the objective compounds (64 mg) as white solid.

$^1$H NMR (DMSO-$d_6$) δ: 7.58(dd, 1H), 7.07(br.s, 1H), 6.98(br.s, 1H), 6.03(t, 0.38H), 5.95(dd, 0.62H), 5.70(m, 1H), 4.90(t, 0.38H), 4.07(d, 0.62H), 4.00(d, 0.38H), 3.83(d, 0.38H), 3.77(d, 0.62H), 3.56–3.61(m, 0.76H), 3.42–3.33(m, 1.24H), 3.20(s, 1.20H), 3.06(s, 1.80H), 2.37–2.30(m, 0.38H), 2.27–2.22(m, 0.62H), 1.96–1.88(m, 1H)

EXAMPLE 20 cis-2-(Cytosin-1-yl)-4-fluoro-4-hydroxymethyltetrahydrofuranhydrochloride(28)

cis-2-(Cytosin-1-yl)-4-fluoro-4-hydroxymethyltetrahydrofuran (6 mg) was added to methanolic hydrochloride solution and the resultant mixture was stirred for 20 min. After filtration, the mixture was dried by removing solvent under reduced pressure, and then methanol was added the residue for drying under reduced pressure. The residue was recrystallized in methanol to obtain the objective compound (5 mg) as a white solid.

$^1$H NMR(DMSO-$d_6$) δ: 9.74(br. S, 1H), 8.65(br. S, 1H), 8.01–8.03(d, 1H), 6.13–6.11(m, 1H), 6.07(t, 1H), 4.27–4.15 (m, 1H), 4.08–4.00(m, 1H), 3.73–3.62(m, 2H), 2.60–2.30 (m, 2H)

UV($H_2O$) $\lambda$max: 279, 220(sh) nm

Test of Anti-HBV Activity

The anti-HBV activity of the compounds according to the present invention, was tested in Hep G2 2.2.15 cell lines, as using 2',3'-dideoxycytidine as a control compound. The results are shown in Table 1.

TABLE 1

Anti-HBV activity of the compounds

| Test Compound | $EC_{50}$ (μM) | $EC_{90}$ (μM) | $CC_{50}$ (μM) | SI ($CC_{50}/EC_{90}$) |
|---|---|---|---|---|
| 5 (Example 5) | 0.1 | 0.8 | 472 | 590 |
| 6 (Example 5) | 0.2 | 1.0 | 2,321 | 2,321 |
| 7 (Example 6) | 0.011 | 0.143 | 1,546 | 10,811 |
| 8 (Example 6) | 0.080 | 0.522 | 1,500 | 2,874 |
| 9 (Example 7) | 0.8 | 0.7 | 2,232 | 319 |
| 10 (Example 7) | 0.061 | 0.835 | 955 | 1,444 |
| 15 (Example 10) | 0.6 | 4.4 | 2,203 | 501 |
| 16 (Example 10) | 0.8 | 5.3 | 451 | 85 |
| Control compound | 7.57 | 35.035 | 1,079.443 | 30.811 |

As shown in the Table 1 above, compounds of the present invention have excellent anti-HBV effect with low toxicity.

We claim:

1. A nucleoside derivative represented by the following formula (I):

wherein $R_1$ represents hydrogen, phosphate, phosphonate, alkyl or acyl, $R_2$ represents alkoxy or halogen, $R_3$ represents substituted or non-substituted pyrimidine or purine base, and X represents O, S, SO or $SO_2$; stereoisomers thereof or a mixture of these isomers, and pharmaceutically acceptable salts thereof.

2. A nucleoside derivative according to claim 1, wherein the compound is cis isomer.

3. A nucleoside derivative according to claim 1, wherein the compound is trans isomer.

4. A nucleoside derivative according to claim 1, which is selected from a group consisting of cis-2-(uracil-1-yl)-4- fluoro-4-hydroxymethyltetrahydrofuran, trans-2-(uracil-1-yl)-4-fluoro-4-hydroxymethyltetrahydrofuran, and mixtures thereof; cis-2-(thymin-1-yl)-4-fluoro-4-hydroxymethyltetrahydrofuran, trans-2-(thymin-1-yl)-4-fluoro-4-hydroxymethyltetrahydrofuran, and mixtures thereof, cis-2-(5-fluorouracil-1-yl)-4-fluoro-4-hydroxymethyltetrahydrofuran, trans-2-(5-fluorouracil-1-yl)-4-fluoro-4-hydroxymethyltetrahydrofuran, and mixtures thereof; cis-2-(5-chlorouracil-1-yl)-4-fluoro-4-hydroxymethyltetrahydrofuran, trans 2-(5-chlorouracil-1-yl)-4-fluoro-4-hydroxymethyltetrahydrofuran, and mixtures thereof; cis-2-(5-bromouracil-1-yl)-4-fluoro-4-hydroxymethyltetrahydrofuran, trans-2-(5-bromouracil-1-yl)-4-fluoro-4-hydroxymethyltetrahydrofuran, and mixtures thereof; cis-2-(5-iodouracil-1-yl)-4-fluoro-4-hydroxymethyltetrahydrofuran, trans-2-(5-iodouracil-1-yl)-4-fluoro-4-hydroxymethyltetrahydrofuran, and mixtures thereof; cis-2-[5-(trans-2-bromovinyl)uracil-1-yl]-4-fluoro-4-hydroxymethyltetrahydrofuran, trans-2-[5-(trans-2-bromovinyl)uracil-1-yl]-4-fluoro-4-hydroxymethyltetrahydrofuran, and mixtures thereof; cis-2-(cytosin-1-yl)-4-fluoro-4-hydroxymethyltetrahydrofuran, trans-(2-(cytosin-1-yl)-4-fluoro-4-hydroxymethyltetrahydrofuran, and mixtures thereof; cis-2-(5-fluorocytosin-1-yl)-4-fluoro-4-hydroxymethyltetrahydrofuran trans-2-(5-fluorocytosin-1-yl)-4-fluoro-4-hydroxymethyltetrahydrofuran, and mixtures thereof; cis-2-(5-methylcytosin-1-yl)-4-fluoro-4-hydroxymethyltetrahydrofuran, trans-2-(5-methylcytosin-1-yl)-4-fluoro-4-hydroxymethyltetrahydrofuran, and mixtures thereof; cis-2-(adenin-9-yl)-4-fluoro-4-hydroxymethyltetrahydrofuran, trans-2-(adenin-9-yl)-4-fluoro-4-hydroxymethyltetrahydrofuran, and mixtures thereof; cis-2-(6-hydroxypurin-9-yl)-4-fluoro-4-hydroxymethyltetrahydrofuran, trans-2-(6-bydroxypurin-9-yl)-4-fluoro-4-hydroxymethyltetrahydrofuran, and mixtures thereof; cis-2-(6-methylaminopurin-9-yl)-4-fluoro-4-hydroxymethyltetrahydrofuran, trans-2(6-methylaminopurin-9-yl)-4-fluoro-4-hydroxymethyltetrahydrofuran, and mixtures thereof, cis-2-(6-chloropurin-9-yl)-4-fluoro-4-hydroxymethyltetrahydrofuran, trans-2-(6-chloropurin-9-yl)-4-fluoro-4-hydroxymethyltetrahydrofuran, and mixtures thereof; cis-2-(fluoroadenin-9-yl)-4-fluoro-4-hydroxymethyltetrahydrofuran, trans-2-(2-fluoroadenin-9-yl)-4-fluoro-4-hydroxymethyltetrahydrofuran, and mixtures thereof; cis-2-(2-amino-6-chloropurin-9-yl)-4-fluoro-4-hydroxymethyltetrahydrofuran, trans-2-(2-amino-6-chloropurin-9-yl)-4-fluoro-4-hydroxymethyltetrahydrofuran, and mixtures thereof; cis-2-(guanin-9-yl)-4-fluoro-4-hydroxymethyltetrahydrofuran, trans-2-(guanin-9-yl)-4-fluoro-4-hydroxymethyltetrahydrofuran, and mixtures thereof; cis-2-(thymin-1-yl)-4-methoxy-4-hydroxymethyltetrahydrofuran, trans-2-(thymin-1-yl)-4-methoxy-4-hydroxymethyltetrahydrofuran, and mixtures thereof; cis-2-(cytosin-1-yl)-4-methoxy-4-hydroxymethyltetrahydrofuran, trans-2-(cytosin-1-yl)-4-methoxy-4-hydroxymethyltetrahydrofuran, and mixtures thereof; and pharmaceutically acceptable salts of these compounds.

5. A nucleoside derivative according to claim 1, which is in the form of hydrochloric acid salt.

6. A nucleoside derivative according to claim 1, which is in the form of a racemic mixture.

7. A nucleoside derivative according to claim 1, which is in the form of an optically pure enantiomer.

8. A compound represented by the following formula (IV):

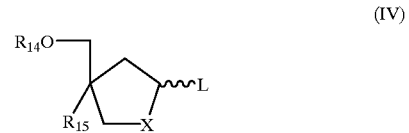

wherein $R_{14}$ represents hydrogen or protective group for hydroxyl group; $R_{15}$ represents alkoxy or halogen; L represents acyloxy, halide or alkoxy group; and X represents O, S, SO or $S_2$; structural or stereoisomers thereof, and the mixture of these isomers.

9. A process for preparing a compound represented by general formula (I) which comprises the step of reacting a compound represented by formula (IV) with a base ($R_3H$) in the presence of a Lewis acid;

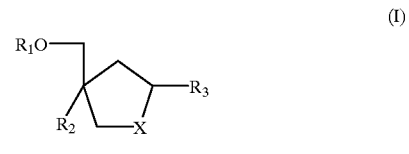

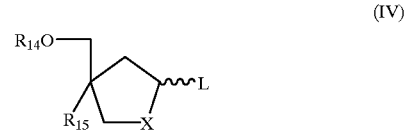

wherein $R_1$ represents hydrogen, phosphate, phosphonate, alkyl or acyl; $R_2$ represents alkoxy or halogen; $R_3$ represents substituted or non-substituted pyrimidine or purine base; and X represents O, S, SO or $SO_2$; $R_{14}$ represents hydrogen or protective group for hydroxyl group; $R_{15}$ represents alkoxy or halogen; and L represents acyloxy, alkoxy group or halide.

10. A process according to claim 9, wherein the compound (I) is obtained as an optically pure enantiomer.

11. A nucleoside derivative according to one of claims 1 to 3, in which $R_3$ of the formula (I) is selected from the following groups:

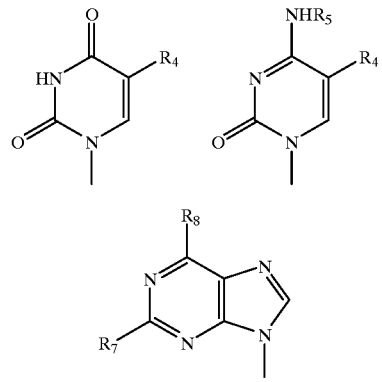

wherein $R_4$ represents hydrogen, saturated alkyl, unsaturated alkyl, substituted saturated alkyl, substituted unsaturated alkyl, or halogen; $R_5$ represents hydrogen, hydroxy, alkoxy, saturated alkyl, unsaturated alkyl, substituted saturated alkyl, substituted unsaturated alkyl, saturated acyl, unsaturated acyl, substituted saturated acyl, or substituted unsaturated acyl; and $R_7$ and $R_8$ each represents hydrogen, hydroxy, amino, or halogen.

12. A nucleoside derivative according to one of claims 1 to 3, in which $R_1$ represents hydrogen, phosphate or phosphonate; $R_2$ represents alkoxy or halogen; X represents O or S; and $R_3$ represents groups represented by the following formulas:

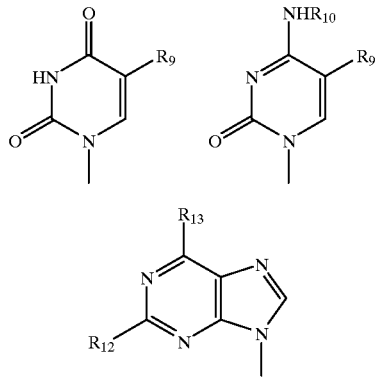

wherein $R_9$ represents hydrogen, methyl, hydroxymethyl, methoxymethyl, methylthiomethyl, trifluoromethyl, ethyl, propyl, cyclopropyl, vinyl, 2-bromovinyl, fluoro, chloro, bromo or iodo; $R_{10}$ represents hydrogen, methyl, ethyl, hydroxy, methoxy or $C_1$–$C_{16}$ acyl; and $R_{12}$ and $R_{13}$ each represents hydrogen, hydroxy, amino, fluoro, chloro, bromo or iodo.

13. A compound represented by the following formula (I):

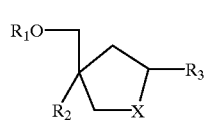
(I)

wherein $R_1$ represents hydrogen, phosphate, phosphonate, alkyl or acyl; $R_2$ represents alkoxy or halogen; X represents O, S, SO, or $SO_2$; and $R_3$ represents groups represented by the following formulas:

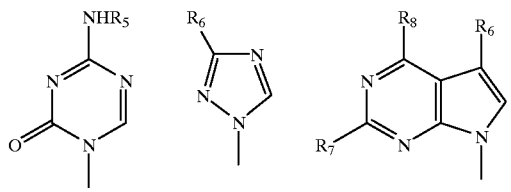

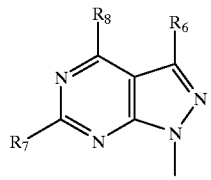

wherein $R_5$ represents hydrogen, hydroxy, alkoxy, saturated alkyl, unsaturated alkyl, substituted saturated alky, substituted unsaturated alkyl, saturated acyl, unsaturated acyl, substituted saturated acyl, or substituted unsaturated acyl; $R_6$ represents hydrogen, cyano, carboxyl, alkoxycarbonyl, carbamoyl or thiocarbamoyl; and $R_7$ and $R_8$ each represents hydrogen, hydroxy, amino, or halogen; stereoisomers thereof or a mixture of these isomers, and pharmaceutically acceptable salts thereof.

14. A compound according to claim 13 which $R_1$ represents hydrogen, phosphate or phosphonate; $R_2$ represents alkoxy or halogen; X represents O or S; and $R_3$ represents groups represented by the following formulas:

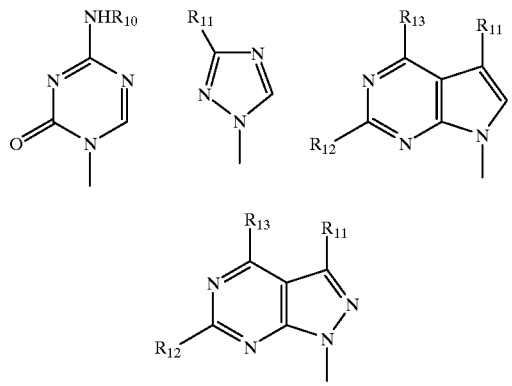

wherein $R_9$ represents hydrogen, methyl, hydroxymethyl, methoxymethyl, methylthiomethyl, trifluoromethyl, ethyl, propyl, cyclopropyl, vinyl, 2-bromovinyl, fluoro, chloro, bromo or iodo; $R_{10}$ represents hydrogen, methyl, ethyl, hydroxy, methoxy or $C_1$–$C_{16}$ acyl; $R_{11}$ represents hydrogen, cyano, carboxyl, alkoxycarbonyl, carbamoyl or thiocarbamoyl; and $R_{12}$ and $R_{13}$ each represents hydrogen, hydroxy, amino, fluoro, chloro, bromo or iodo.

15. A compound according to claim 13, which is selected from a group consisting of cis-2-(3-carbamoyl-1,2,4-triazol-1-yl)-4-fluoro-4-hydroxymethyltetrahydrofuran, trans-2-(3-carbamoyl-1,2,4-triazol-1-yl)-4-fluoro-4-hydroxymethyltetrahydrofuran; cis-2-(3-carbamoyl-1,2,4-triazol-1-yl)-4-methoxy-4-hydroxymethyltetrahydrofuran; trans-2-(3-carbamoyl-1,2,4-triazol-1-yl)-4-methoxy-4-hydroxymethyltetrahydrofuran.

* * * * *